United States Patent
Corcoran et al.

(10) Patent No.: US 7,115,135 B2
(45) Date of Patent: Oct. 3, 2006

(54) OCCLUSION DEVICE HAVING FIVE OR MORE ARMS

(75) Inventors: Michael P. Corcoran, Oakdale, MN (US); Joseph A. Marino, Apple Valley, MN (US)

(73) Assignee: Cardia, Inc., Eagan, MN (US)

( * ) Notice: Subject to any disclaimer, the term of this patent is extended or adjusted under 35 U.S.C. 154(b) by 254 days.

(21) Appl. No.: 10/348,701

(22) Filed: Jan. 22, 2003

(65) Prior Publication Data
US 2004/0143291 A1 Jul. 22, 2004

(51) Int. Cl.
*A61B 17/00* (2006.01)
*A61B 17/08* (2006.01)

(52) U.S. Cl. .................................. 606/151; 606/153
(58) Field of Classification Search ............... 606/151, 606/152, 153, 154–155, 200
See application file for complete search history.

(56) References Cited

U.S. PATENT DOCUMENTS

| | | | |
|---|---|---|---|
| 3,874,388 A | 4/1975 | King et al. | |
| 4,007,743 A | 2/1977 | Blake | 128/334 |
| 4,917,089 A | 4/1990 | Sideris | 606/215 |
| 5,108,420 A | 4/1992 | Marks | 606/213 |
| 5,171,259 A | 12/1992 | Inoue | 606/213 |
| 5,284,488 A | 2/1994 | Sideris | 606/213 |
| 5,334,137 A | 8/1994 | Freeman | 604/8 |
| 5,334,217 A | 8/1994 | Das | 606/213 |
| 5,397,331 A | 3/1995 | Himpens et al. | 606/151 |
| 5,425,744 A | 6/1995 | Fagan et al. | 606/213 |
| 5,433,727 A | 7/1995 | Sideris | 606/213 |
| 5,451,235 A | 9/1995 | Lock et al. | 606/213 |
| 5,634,936 A | 6/1997 | Linden et al. | 606/213 |
| 5,702,421 A | 12/1997 | Schneidt | 606/213 |
| 5,709,707 A | 1/1998 | Lock et al. | 606/213 |
| 5,725,552 A | 3/1998 | Kotula et al. | 606/213 |
| 5,741,297 A | 4/1998 | Simon | 606/213 |
| 5,904,703 A | 5/1999 | Gilson | 606/213 |
| 5,944,738 A * | 8/1999 | Amplatz et al. | 606/213 |
| 6,024,756 A | 2/2000 | Huebsch et al. | 606/213 |
| 6,077,291 A * | 6/2000 | Das | 606/213 |
| 6,174,322 B1 * | 1/2001 | Schneidt | 606/213 |
| 6,206,907 B1 | 3/2001 | Marino et al. | 606/215 |
| 6,379,368 B1 | 4/2002 | Corcoran et al. | 606/153 |

FOREIGN PATENT DOCUMENTS

| | | |
|---|---|---|
| DE | 233 303 | 2/1986 |
| DE | 42 22 291 C1 | 1/1994 |
| EP | 0 362 113 | 4/1993 |
| EP | 0 541 063 | 9/1998 |
| GB | 2 269 321 A | 9/1994 |

* cited by examiner

*Primary Examiner*—Vy Q Bui
(74) *Attorney, Agent, or Firm*—Kinney & Lange, P.A.

(57) ABSTRACT

An occlusion device having at least five arms. Though the number of arms is increased, the diameter of each arm is reduced. As a result, the increased number of arms provides the desired tension as the occlusion device is deployed and provides the desired strength to hold the occlusion device in place and properly occlude the defect. At the same time, the reduced diameter of the arms improves the cycle life of the occlusion device. Furthermore, the increased number of arms provides for better sealing across the defect and reduces residual shunting.

42 Claims, 6 Drawing Sheets

OCCLUSION DEVICE HAVING FIVE OR MORE ARMS

CROSS-REFERENCE TO RELATED APPLICATION(S)

This application is related to U.S. Patent application entitled Articulated Center Post, Ser. No. 10/348,856, U.S. Pat. application entitled Hoop Design for Occlusion Device, Ser. No. 10/349,118, Septal Stabilization Device, Ser. No.10/349,744, and U.S. Pat. application entitled Laminated Sheets for Use in a Fully Retrievable Occlusion Device, Ser. No. 10/348,864, all filed on even date herewith.

BACKGROUND OF THE INVENTION

The present invention relates to a method of occluding an aperture in a body. More specifically, the present invention relates to an occlusion device for occluding a septal defect having five or more arms.

The heart is generally comprised of four chambers, the left and right atrium and the left and right ventricle. Separating the left and right sides of the heart are two walls, or septa. The wall between the two atria is the interatrial septum, and the wall between the two ventricles is the interventricular septum. There are several defects which can affect the septa of both children and adults, including patent ductus arteriosus, patent foramen ovate, atrial septal defects (ASDs), and ventricular septal defects (VSDs).

Normally, permanently repairing septal or other cardiac defects in adults and children requires open heart surgery, a high risk, painful, and costly procedure. In response to these concerns, modern occlusion devices have been developed are that small enough to be delivered through a catheter. Rather than surgery, these occlusion devices are deployed by inserting a catheter into a major blood vessel and moving the occlusion device through the catheter. This type of procedure can be performed in a cardiac cathlab, and avoids much of the risks, cost, and pain associated with open heart surgery. These modern occlusion devices can be used to treat a wide range of cardiac defects, including patent ductus arteriosis, patent foramen ovale, atrial septal defects, ventricular septal defects, and can be used to occlude other cardiac and non-cardiac apertures.

Occlusion devices that can be inserted via a catheter include button devices, collapsible umbrella-like structures, and plug-like devices. Occlusion devices with umbrella-like structures use a system of small metal wires to hold the occlusion device in place. When designing such occlusion devices, there are several design constraints due to the severe environment the human heart presents, including a continuous cycling of up to 5 billion pulses over the lifetime of a human.

First, the occlusion device must be stiff enough and have enough tension so that the occlusion device will remain in place even as the heart pulses. Second, the occlusion device must have a high cycle life, so that it does not develop fatigue failure problems due to the constant flexing of portions of the occlusion device caused by the beating heart. Lastly, the device must have a suitable tactile response so that when it is deployed, the physician can "feel" whether or not the device has been successfully deployed at the defect.

Each of these constraints competes with the other, making it difficult to design an occluder which adequately addresses all of them. Increasing stiffness may increase the tactile response, but may also lead to a decreased cycle life. This is because increasing the stiffness typically involves varying the shape and increasing the diameter of the wires used in occlusion devices. However, increasing the diameter of the wire to improve its stiffness or strength often reduces the cycle life because a larger diameter wire is often more brittle, and thus more susceptible to fatigue failure. Conversely, using smaller, thinner wires may result in increase fatigue life, but may also reduces the ability of the occlusion device to successfully occlude the defect, and may adversely affect the tactile response felt by the physician.

Yet another design criteria for designing an occlusion device is to ensure that the occluder seats properly. Because every patient's heart is different, and because it is extremely rare for the surfaces of the heart to be smooth and even, it is difficult to ensure that the occlusion device properly matches the contours of the defect to be occluded.

Thus, there is a need in the art for an occlusion device with a high fatigue life that has enough tension so that the occlusion device stays in place and provides the desired feel to a physician. There is also a need in the art for improved conformance to the defect to be occluded.

BRIEF SUMMARY OF THE INVENTION

The present invention is an improved occlusion device for occluding a septal defect. The occlusion device is comprised of a center section to which upper and lower wire fixation devices are attached. Attached to the upper and lower fixation devices are polyvinyl alcohol sails which serve to further occlude the defect. To prevent any damage to surrounding tissue, the fixation devices are fitted with atraumatic tips. When deployed, the center post extends through the defect, and the upper fixation device and upper sheet are positioned one side of a defect, and the lower fixation device and lower sails are located on the other side of the defect. The upper and lower fixation devices are formed to bias the sails toward the wall of the defect so that the sails occlude the defect.

The upper and lower fixation devices comprise at least five arms. Forming the upper and lower fixation devices with at least five arms improves the tension and "feel" of the device as it is deployed across the defect. At the same time, the diameter of each of the arms is decreased to make them more flexible and increase their fatigue life. As a result, increasing the number of arms provides the desired tension as the occlusion device is deployed, provides the desired strength to hold the occlusion device in place and properly occlude the defect, but yet also provides the desired fatigue life of the occlusion device. Furthermore, the increased number of arms on the upper and lower fixation devices provides for better sealing across the defect and reduces residual shunting.

DETAILED DESCRIPTION

Figure 1:
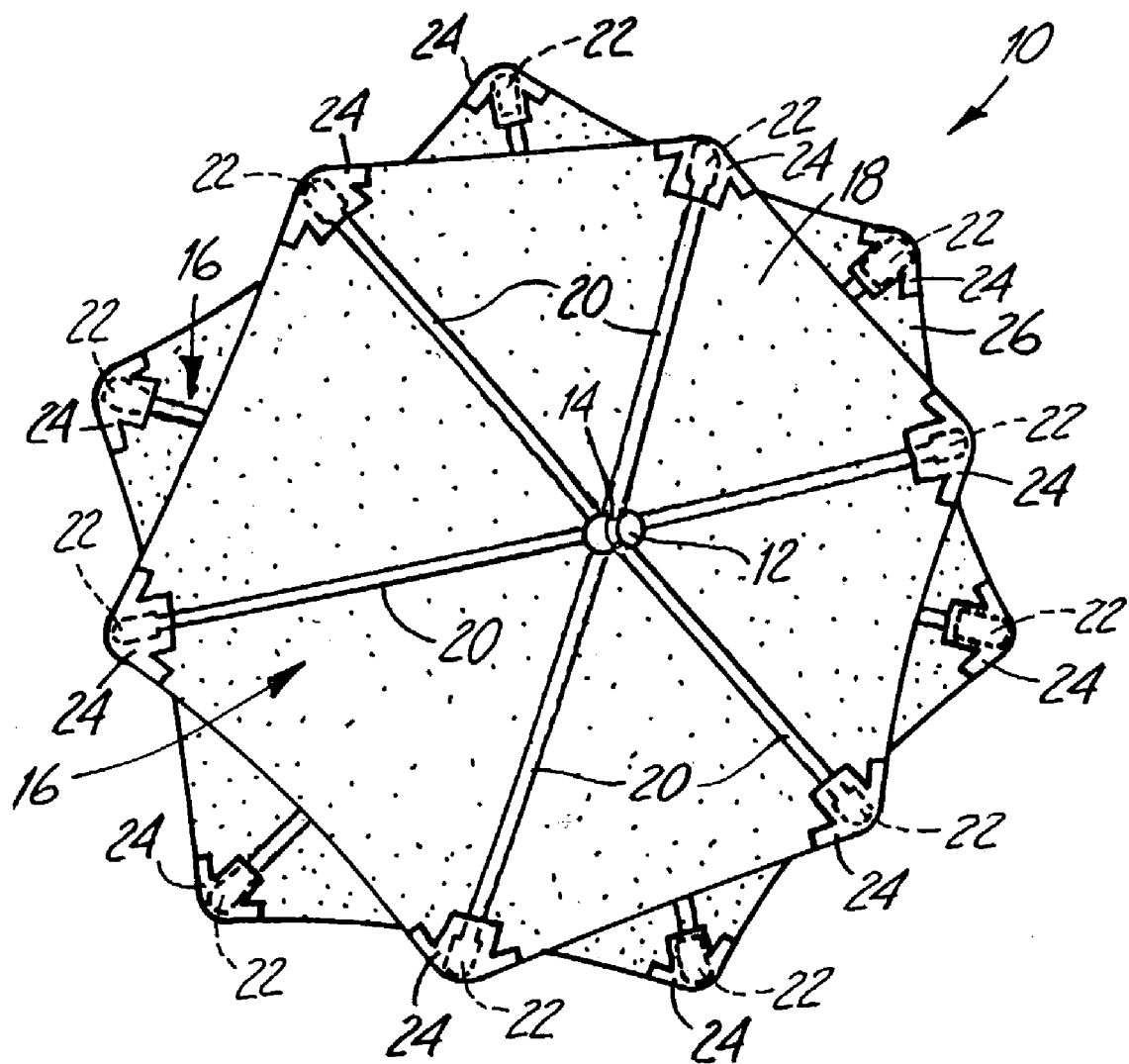
FIG. 1 is a perspective view of an occlusion device according to the present invention.

FIG. 1 is a top perspective view of one embodiment of an occlusion device 10. The occlusion device 10 comprises a center section 12 having a groove 14, an upper wire fixation device 16, and an upper sail 18. The upper wire fixation device 16 comprises six wire arms 20 which terminate in atraumatic tips 22. The atraumatic tips 22 are covered by reinforcement patches 24. Also visible in FIG. 1 is a bottom sail 26 and wire arms 28, which likewise terminate in atraumatic tips 22 covered by patches 24.

Figure 2:
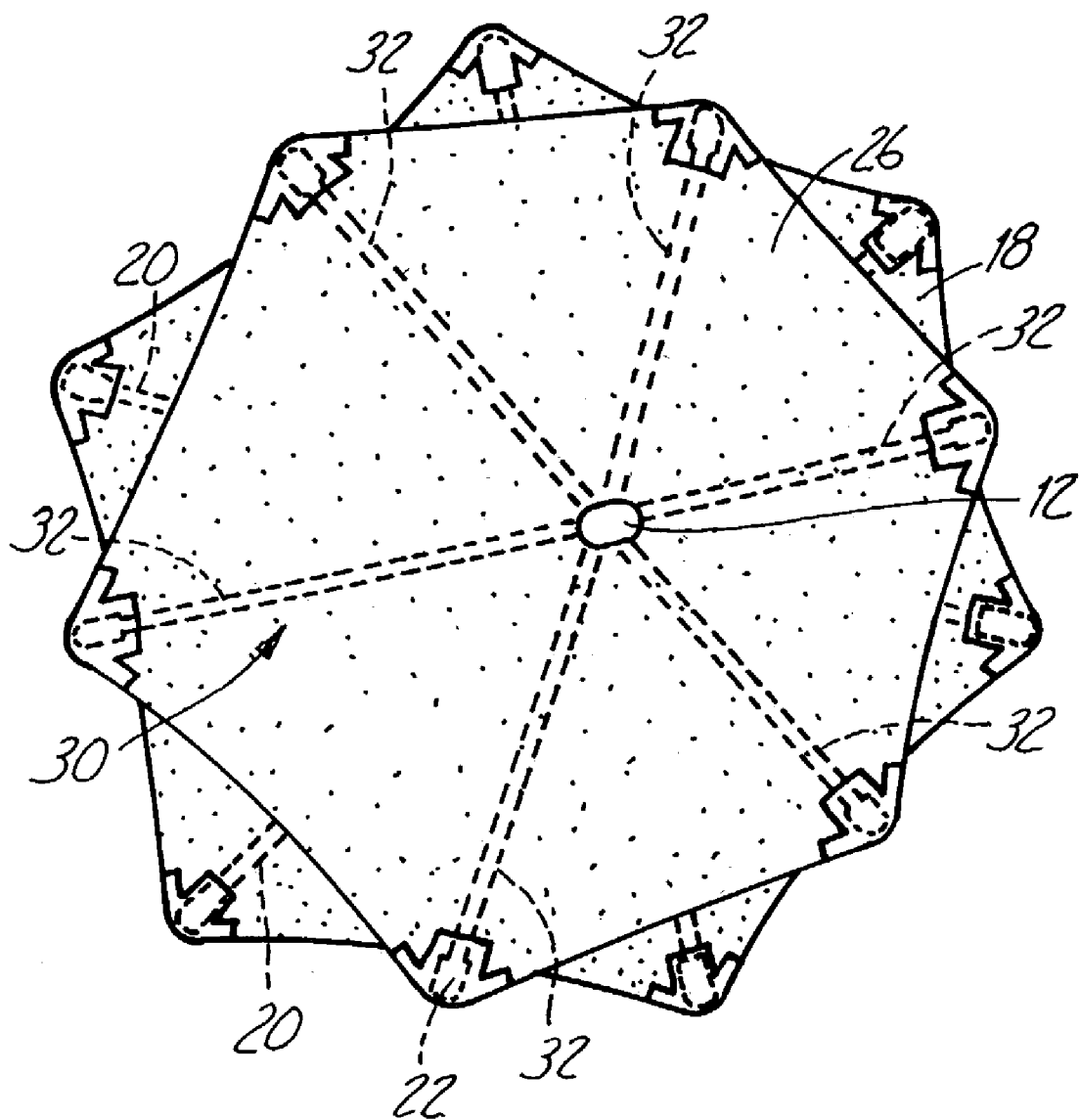
FIG. 2 is a top view of a six-arm occlusion device.

FIG. 2 is a bottom perspective view of the occlusion device 10. Shown in FIG. 2 is the center post 12, bottom sail 26 and lower fixation device 30. The lower fixation device 30 likewise comprises six wire arms 32 which terminate in atraumatic tips 22 covered by reinforcement patches 24. Also shown in FIG. 2 is the upper sail 18, portions of the wire arms 20 and the atraumatic tips 22 covered by reinforcement patches 24.

Unlike the upper fixation device 16 which is located on an outer side of the upper sail 18, the lower fixation device 30 is located on an inner side of the lower sail 26. However, the device is not so limited, and the fixation devices 16, 30 may be located on the outer side of the sails 26, 18, on the inner side of the sails 26, 18, or any combination thereof.

The upper and lower fixation devices 16, 30 are connected to the center post 12 using any suitable method, including welding, soldering, or adhesives. One method of connecting upper and lower fixation devices 16, 30 to the center post 12 is to provide the center post 12 with drill holes through which the upper and lower fixation devices 16, 30 extend. To hold the fixation devices 16, 30 more securely, the fixation devices 16, 30 may additionally be welded, soldered, or otherwise attached to the center post 12 in a more permanent manner.

When connected to the center post 12 using holes drilled through the center post 12, the fixation devices 16, 30 may be formed of three wires. The three wires create the six arms 20, 32 because each wire forms two arms 20, 32 when the wire passes through the center post 12. The atraumatic tips 22 are located at the distal end of each arm 20, 32 and serve to minimize damage to the surrounding tissue. Though not shown, the center post 12 may comprise an articulation to allow the device 10 to conform to a wider variety of defects.

The sails 18, 26 are connected to the occlusion device 10 at the center post and at the upper and lower fixation devices 16, 30. The sails 18, 26 may be connected to the fixation devices 16, 30 using any suitable method. One method of attaching the sails 18, 20 to the fixation devices 16, 30 is to suture the sails 18, 20 to the fixation devices 16, 30 along the length of the arms 20, 32. Alternatively, the sheets 18, 20 may be sewn to device 10 at the atraumatic tips 22. To do so, the atruamatic tips 22 may be provided with drilled holes through which sutures can pass to sew the sheets 18, 20 to the tips 22.

The reinforcement patches 24 are configured to fit over the atraumatic tips 22. The reinforcement patches 24 are placed at the end of an tips 22 and are folded over the tips 22 so that the tips 22 are covered on both their top and bottom sides. The patches 24 may be secured to the sheets 18, 26 using any suitable method, including sutures, heat treatment, or laminating.

The reinforcement patches 24 serve to reinforce the foam sheets 18, 26 near the ends of the wire arms 20, 32. This reinforcement helps strengthens the sails 18, 26 at the locations they are likely to tear or wear. The reinforcement patches also act as a cushion between the metal tips 22 of the occlusion device 10 and the tissue surrounding the defect. The patches provide extra protection of the tissue from the pressure that the device 10 exerts on the tissue at the atraumatic tips 22.

The occlusion device 10 is configured to be deployed through a catheter, and the groove 14 on the center section 12 is configured to allow the occlusion device 10 to be grasped by a forceps as it is guided through the catheter. More specifically, the occlusion device 10 is constructed so that the upper and lower fixation devices 16, 30 are easily collapsible about the center section 12. Due to this construction, the occlusion device 10 can be folded so that the upper fixation device 16 is folded upwards in the axial direction and the lower fixation device 30 is folded downwards in the axial direction. The upper and lower sails 18, 26 attached to the upper and lower fixation devices 16, 30 are also flexible, and can likewise collapse as the upper and lower devices 16, 30 are folded.

The occlusion device 10 is preferably made from bio-compatible materials with the desired properties. More specifically, the wire fixation devices 16, 30 are preferably formed of a material that is capable of shape memory. One such suitable material is a nickel-titanium alloy, commonly called Nitinol. Nitinol is preferably used because it is commercially available, very elastic, non-corrosive, and has a fatigue life greater than that of stainless steel. Similarly, the center post 12 may be formed of platinum iridium, the atraumatic tips 22 may be formed of titanium, and any sutures may be formed of polypropylene, all of which are bio-compatible.

The sails 18, 26, also called sheets 18, 26, are comprised of a medical grade polymer in the form of film, foam, gel, or a combination thereof. One suitable material is DACRON®. Preferably, a high density polyvinyl alcohol (PVA) foam is used, such as that offered under the trademark IVALON®. To minimize the chance of the occlusion device 10 causing a blood clot, the foam sails 18, 26 may be treated with a thrombosis inhibiting material. One such suitable material is heparin.

In some instances, it may be desirable to form the sheets 18, 26 so that they are not both the same size. For instance, one sheet and its associated fixation device can be made smaller than the corresponding sheet and its associated fixation device. This is particularly useful in situations where the occlusion device 10 is to be placed at a location in the heart which is close to other nearby cardiac structures. Making the sails 18, 26 different sizes may assist in providing optimal occlusion of a defect, without affecting other structures of the heart which may be nearby.

To ensure the occlusion device 10 is effective at closing a septal defect even after it has been passed through a catheter, the wire arms 20, 32 are preferably subjected to a precise pre-shaping to give them a "shape memory." The pre-shaping can be done either by machining, heat treatment, or both. The shape memory helps to hold the strands together and can be used to add pre-tension to the wire arms 20, 32 so that they remember their shape even after the strong deformation that occurs when the occlusion device 10 is passed through the catheter.

In the past, occlusion devices have suffered from fatigue failures, such as cracks or breaks, due to the extreme environment the human heart poses. The human heart may pulse up to 5 billion times over its lifetime, and with each pulse, the wire fixation devices 16, 30 of the occlusion device 10 may undergo flexing or bending. This flexing and bending may eventually lead to the wires experiencing fatigue failure. To avoid fatigue failure of the fixation devices 16, 30, one embodiment of the present invention relies on making the wire fixation devices 16, 30 of stranded wire or cables. The stranded wire or cable improves the fatigue life of the fixation devices 16, 30 without increasing their size or decreasing their strength. The atraumatic tips 22 cap the wire arms 20, 32 and can serve to prevent potential unraveling of the strands in addition to preventing damage to surrounding issue.

A more significant feature of the invention is the number of arms 20, 32 provided on the upper and lower fixation devices 16, 30. The occlusion device 10 is provided with an increased number of arms 20, 32, but the stiffness and tension of each arm 20, 32 is decreased. One method of decreasing the stiffness and tension of each arm is to decrease the diameter of the wire, stranded wires, or cable that form each arm 20, 32. When formed of stranded wire or cables, the individual strands which make up the stranded wire or cable may range in diameter from about 0.001 inches to about 0.15 inches. The overall diameters of the arms 20, 32, even when formed of stranded wire, may range from as small as about 0.003 inches to about 0.050 inches.

In the past, occlusion devices were typically made having only four arms. Each arm had to be flexible enough to be inserted into a catheter, yet stiff enough to firmly occlude the defect. In addition, the arms had to be thin enough to allow the device to fit into a catheter, yet thick enough to provide the desired stiffness. One continuing challenge faced in making the four arm devices was ensuring that the arms did not reach fatigue failure and break. Efforts to prevent fatigue failure involved increasing the diameter of the wire. However, this often led to more brittleness in the arms, and thus a decrease in cycle life. Finally, if the arms were made too flexible, to improve their fatigue life, the device was more difficult to deploy because the tension was low and it was difficult for a physician to "feel" the point where the device was deployed. In addition, if the arms were too flexible, it was possible for the device to embolize.

The present invention addresses all these issues. Increasing the number of arms 20, 32 on the occlusion device 10 ensures that the fixation devices 16, 30 have the required strength or stiffness to hold the sails 18, 26 firmly against the defect. Increasing the number of arms 20, 32 also improves the tension and "feel" of the device as it is inserted, which in turn assists the physician and ensures the device is properly inserted on the first try. At the same time, the diameter of each of the arms 20, 32 has been decreased to make them more flexible and 10 increase their cycle life. Decreasing the diameter of each arm 20, 32 ensures that even though the device 10 has more arms 20, 32, the device 10 can still fit in to small diameter catheters for deployment.

Another benefit of the invention is that the device 10 improves the closing ability of the occlusion device 10. Increasing the number of arms 20, 32 on the device 10 allows the device 10 to better conform to the complex surfaces present at many septal defects. Better conformance of the device 10 to the defect not only improves the functioning of the device, it can also reduce the stress placed on any one of the arms 20, 32. Reducing the stress on the arms 20, 32 also improves the cycle life of the occlusion device 10.

Each arm 20, 32 may be equally spaced from an adjacent arm in the six arm device 10, each arm 20, 32 is located 60° from the adjacent arm. In addition, to assist in maximizing the occlusion ability of the six arm device 10, the upper sail 18 may be offset from the bottom sail 26. The amount one sail is offset from the other may vary based on the desired performance of the device 10. In one embodiment, the upper sail 18 is offset from the bottom sail 26 at an angle of about 30°.

Figure 3:
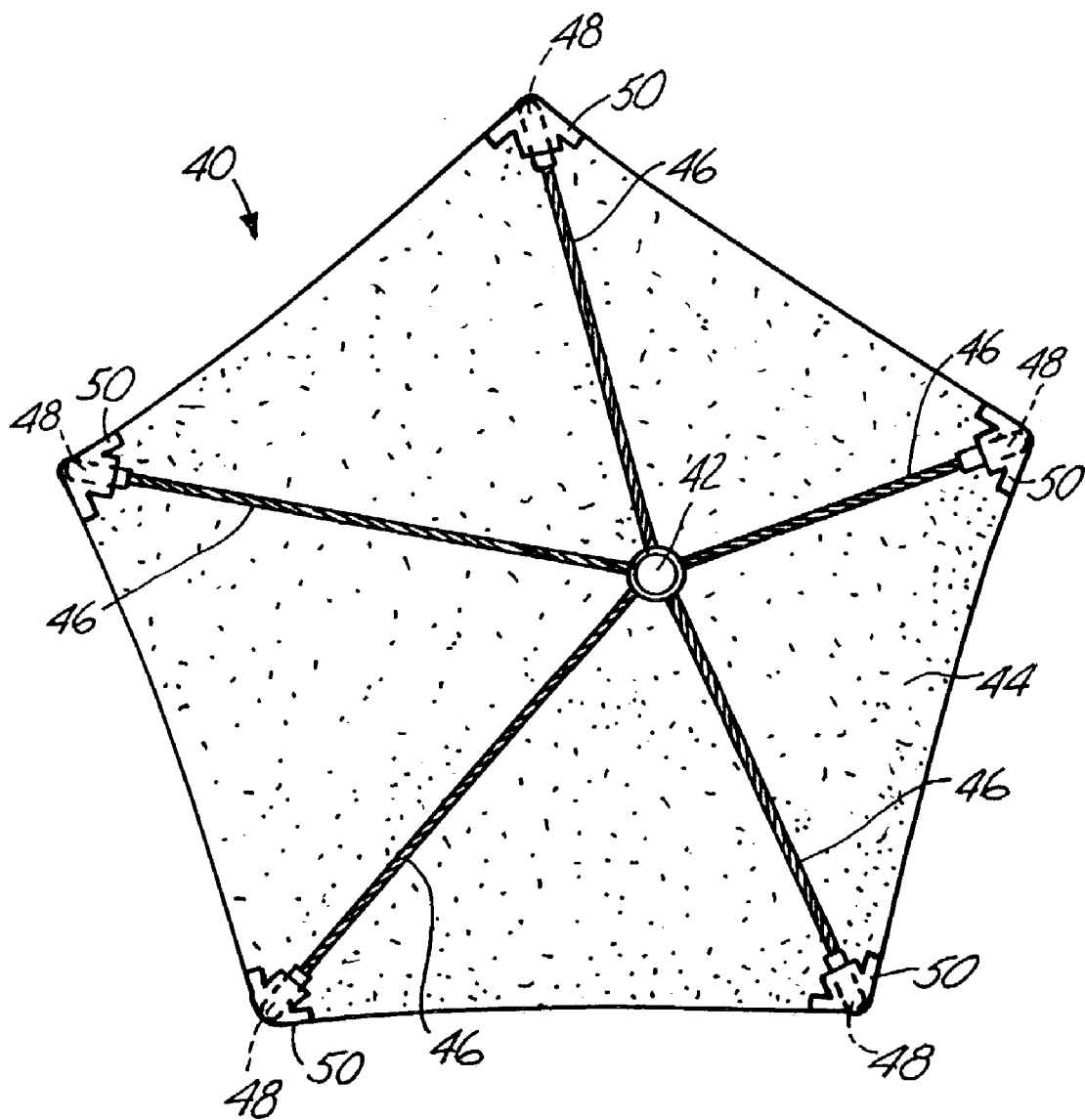
FIG. 3 is a plan view of a portion of a five-arm occlusion device.

FIG. 3 is a top plan view of another example of an occlusion device 40 according to the present invention. The occlusion device 40 comprises a center post 42, sail 44, stranded wire arms 46, end caps 48, and reinforcement patches 50 placed over the tips 48. For simplicity, the occlusion device 40 is shown with only one sail 44. Similar to the occlusion device of FIGS. 1 and 2, the sail 44 is connected to the occlusion device 40 using any suitable method, such as sutures along the arms 46. End caps 48 serve to prevent tissue damage and reinforcement patches 50 both provide extra protection to surrounding tissue and reinforce the sail 44 at the location it is most likely to tear.

The occlusion device 40 of FIG. 3 comprises five arms 46. When forming a five arm device 40, rather than using a single long wire to form two arms by passing the wires through holes in the center post, the five arm device may be formed of five separate short wires. Or, the arms 46 may be formed with a combination of long wires which form two arms and short wires which form single arms. This holds true for all occlusion devices having greater than five arms. For occlusion devices having an odd number of arms, the arms may likewise be created using an odd number of shorter single wires, or may be formed using a combination of long wires which form two arms and short wires which form single arms. Conversely, forming an occlusion device having an even number of arms can be accomplished by using long wires which form two arms, as described with reference to FIGS. 1 and 2 above. The arms 46 are affixed to the center post 42 using any suitable method, such as welding, soldering, adhesive, or other.

Each arm 46 of the device 40 is formed of a small enough diameter so that each arm 46 has an increased cycle life, yet the increased number of arms 46 ensures that the device 40 has enough strength and stiffness to properly occlude a defect. The increased number of arms 46 also ensures that the tension felt by a physician is adequate to detect proper deployment of the device. Increasing the number of arms 46 on the device 40 allows the device 40 to better conform to the complex surfaces present at many septal defects. In this manner, the five arm device 40 achieves the same goals as the six arm device 10 of FIGS. 1 and 2.

Once again, each arm 46 may be spaced equally from an adjacent arm 46. In addition, the number of arms 46 may affect the shape of the sail 44. For example, as shown in FIG. 3, it may be preferable to make the sail 44 so that it has the same number of sides as there are arms 46 on the device 40.

Figure 4:
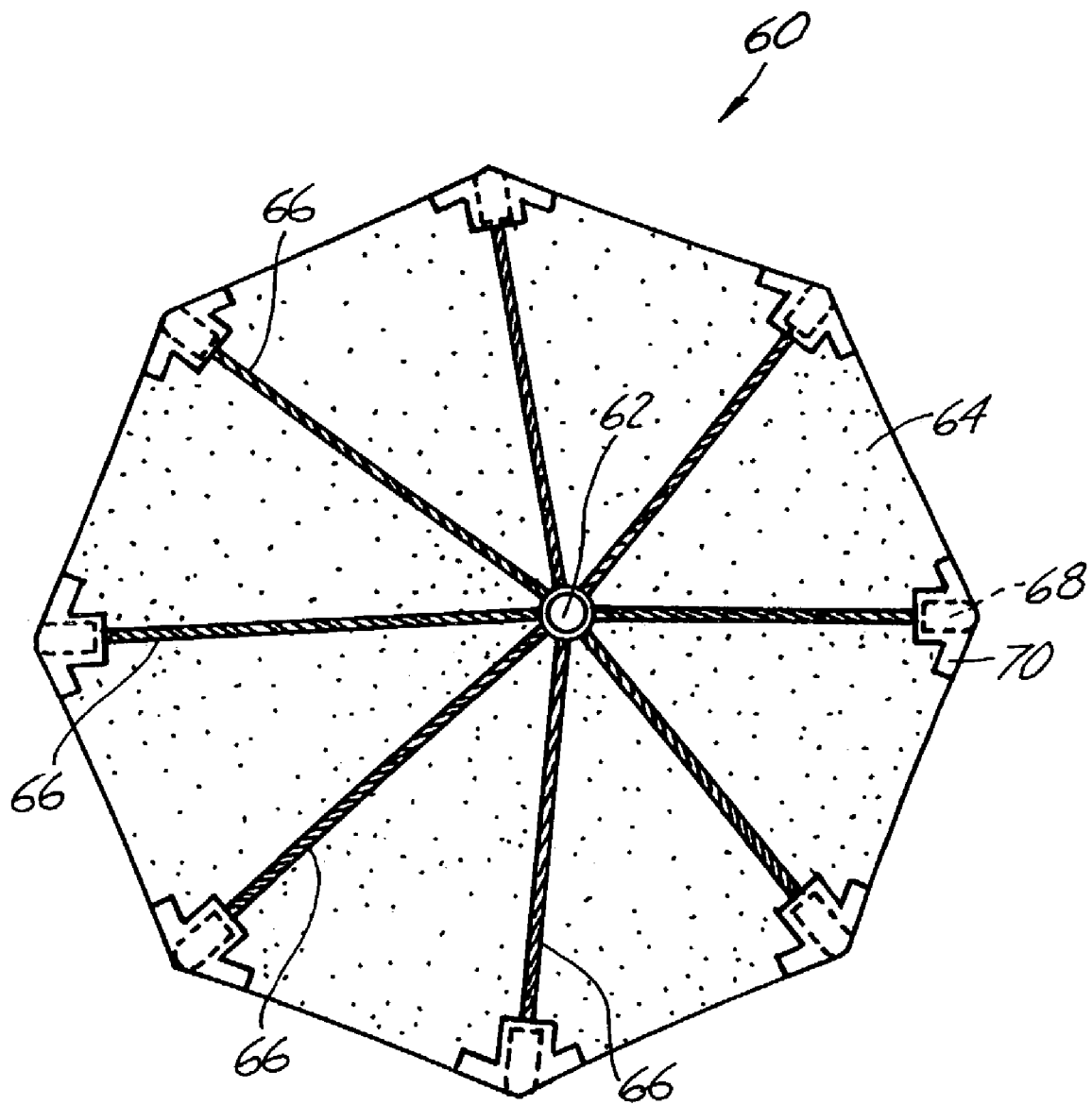
FIG. 4 is a plan view of a portion of an occlusion device having eight arms.

FIG. 4 is a top plan view of yet another example of an occlusion device 60 according to the present invention. The occlusion device 60 comprises a center post 62, sail 64, stranded wire arms 66, end caps 68, and reinforcement patches 70 placed over the tips 68. Just as in FIG. 3, the occlusion device 60 is shown with only one sail 64. Similar to the previously described occlusion devices, the sail 64 is connected to the occlusion device 60 using any suitable method, Such as sutures along the arms 66. End caps 68 serve to prevent tissue damage and reinforcement patches 70 both provide extra protection to surrounding tissue and reinforce the sail 64 at the location it is most likely to tear.

Figure 5:
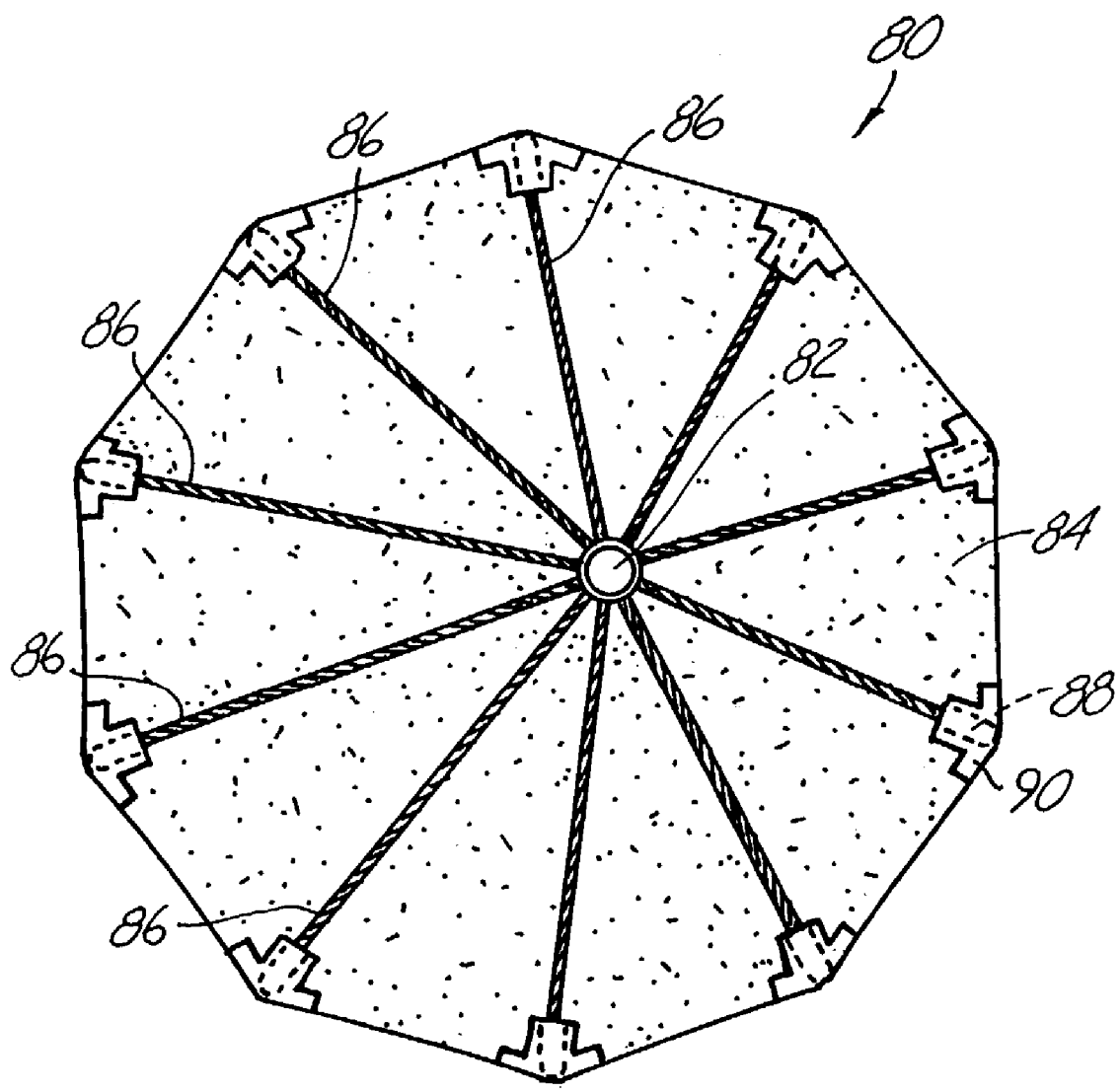
FIG. 5 is a plan view of a occlusion device having ten arms.

FIG. 5 is a top plan view of a final example of an occlusion device 80. The occlusion device 80 comprises a center post 82, sail 84, stranded wire arms 86, end caps 88, and reinforcement patches 90 placed over the tips 88. Just as above, the occlusion device 80 is shown with only one sail 84 for simplicity. Similar to the previously described occlusion devices, the sail 84 is connected to the occlusion device 80 using any suitable method, such as sutures along the arms 86. End caps 88 serve to prevent tissue damage and reinforcement patches 90 both provide extra protection to surrounding tissue and reinforce the sail 84 at the location it is most likely to tear.

The occlusion devices 60, 80 of FIGS. 4 and 5 comprises eight and ten arm devices 60, 80. Though the number of arms 66, 86 is increased, the occlusion devices 60, 80 achieve the same goals as the previously described examples of the invention. Specifically, each arm 66, 86 of the devices 60, 80 are formed of a small enough diameter stranded wire so that each arm 66, 86 has an increased cycle life. At the same time, the increased number of arms 66, 86 ensures that the devices 60, 80 have enough strength and stiffness to properly occlude a defect. The increased number of arms 66, 86 also ensures that the tension felt by a physician is adequate to detect proper deployment of the device. Further, the increased number of arms 66, 86 improves the ability of the devices 60, 80 to conform to the complex surfaces present at many septal defects. In this manner, the devices 60, 80 achieve the same goals as the six arm device 10 of FIGS. 1 and 2.

Once again, each arm 66, 86 may be spaced equally from an adjacent arm 66, 86. In addition, the number of arms 66, 86 may affect the shape of the sails 64, 84. As shown in FIGS. 4 and 5, the sails 64, 84 have the same number of sides as there are arms 66, 86 on the device 60, 80.

Figure 6:
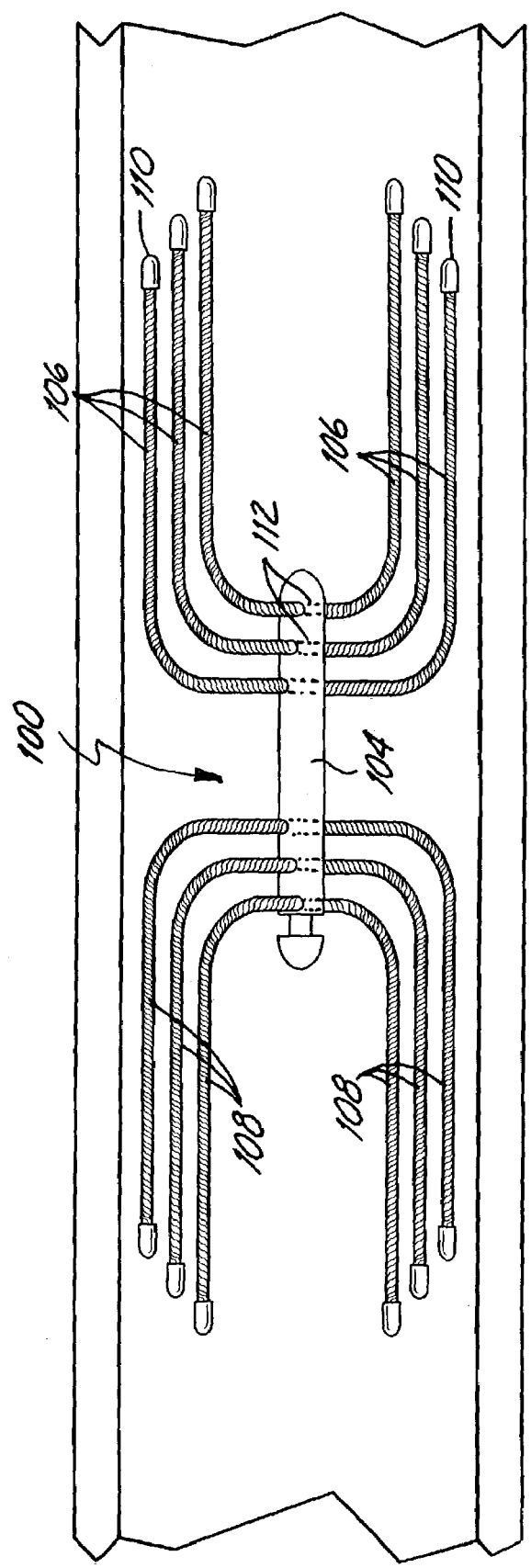
FIG. 6 is a side view of an occlusion device with six arms when the device is inserted into a catheter.

FIG. 6 is a side view of an occlusion device 100 inserted into a catheter 102. The occlusion device 100 comprises a center post 104, six upper arms 106, six lower arms 108, and tips 110. For simplicity, the occlusion device 100 is shown without sails. The upper and lower arms 106, 108 are connected to the center post 104 at holes 112 drilled through the post 104. When inserted into the catheter 102, the upper arms 106 are folded against the catheter 102 in the axial direction of the center post 104. Similarly, the lower arms 108 are folded against the catheter 102 in an opposite direction in the axial direction of the center post 104.

When the occlusion device 100 is inserted into the catheter 102 it is important to ensure that the arms 106, 108 are not of a length that results in the tips 110 clustering at the same location. If the tips 110 all occur at the same location when the device 100 is inside the catheter 102, the device will become too bulky to allow it to be easily moved through the catheter.

One solution for avoiding this problem is to insert the arms 106, 108 at different locations along the length of the center post 104. When connecting the arms 106, 108 to the center post using holes 112, it is possible to space the holes to minimize the clustering of the tips 110 at one location when the arms 106, 108 are folded. Another way to avoid this problem is to make the arms 106, 108 of varying lengths. As is greatly exaggerated in FIG. 6, each set of arms 106, 108 can be made of a different length, allowing all the arms 106, 108 to easily fold and fit into the catheter 102.

In some situations, the occlusion device 100 is not properly deployed and must be retrieved into the catheter 102 after both the upper and lower arms 106, 108 have been pushed out of the catheter 102. The occlusion device 100 may be retrieved by grasping the center post 104 or by grasping any one of the arms 106, 108. When the device 100 is retrieved into the catheter 102, both the upper arms 106 and the lower arms 108 will be folded in the same direction. In such an instance, it is likewise important to vary the length of the upper arms 106 from the length of the lower arms 108 so that when the device is retrieved, the tips 110 on both the upper arms 106 do not cluster at the same location as the tips 110 on the lower arms 108. Thus, though not readily apparent from FIG. 6, the upper arms 106 are of a different length than the lower arms 108.

Although the present invention has been described with reference to preferred embodiments, workers skilled in the art will recognize that changes may be made in form and detail without departing from the spirit and scope of the invention. In particular, any of the applicable features disclosed in related applications U.S. patent application entitled Articulated Center Post, Ser. No. 10/348,856, U.S. Pat. application entitled Hoop Design for Occlusion Device, Ser. No. 10/349,118, Septal Stabilization Device, Ser. No. 10/349,744, and U.S. Pat. application entitled Laminated Sheets for Use in a Fully Retrievable Occlusion Device, Ser. No. 10/348,864, filed on even date herewith, may be of use in the present invention. Each of these applications is hereby incorporated by reference.

The invention claimed is:

1. An improved occlusion device, the occlusion device comprising:
   a center post;
   first and second fixation devices connected to the center post and having an open configuration and a folded configuration, the first and second fixation devices comprising at least five arms, each arm including an atraumatic tip at an outer end, wherein the arms of at least one fixation device are not all of equal length so that when the fixation devices are in a folded configuration the atraumatic tips do not cluster at a same location, and wherein the arms are generally straight and extend radially outward from the center post when the fixation devices are in an open configuration; and
   first and second sheets attached to the first and second fixation devices respectively.

2. The occlusion device of claim 1 wherein a length of the arms of the first fixation device is not equal to a length of the arms of the second fixation device.

3. The occlusion device of claim 2 wherein the arms of the first fixation device do not have equal lengths.

4. The occlusion device of claim 3 wherein the arms of the second fixation device do not have equal lengths.

5. The occlusion device of claim 1 wherein the arms have diameters between about 0.003 inches to about 0.050 inches.

6. The occlusion device of claim 1 wherein the first fixation device is offset at an angle of about 30 degrees from the second fixation device.

7. The occlusion device of claim 1 wherein each arm is spaced at an equal angle from the adjacent arm.

8. The occlusion device of claim 1 wherein the outer perimeter of the sheets correspond to a polygon and the number of sides of the polygon is equal to the number of arms of the fixation devices.

9. The occlusion device of claim 1 wherein the first and second fixation devices comprise six arms.

10. The occlusion device of claim 9 wherein each of the six arms are formed by three wires extending through holes in the center post.

11. An occlusion device with improved seating ability, the occlusion device comprising:
    a center post;
    first and second fixation devices emanating from the center post and having an open configuration and a folded configuration, wherein the first and second fixation devices comprise at least six arms, each arm including an atraumatic tip at an outer end, wherein at least one arm of the first fixation device has a length not equal to a length of the other arms of the first fixation device so that when the fixation devices are in a folded configuration the atraumatic tips do not cluster at a same location, and wherein the arms are generally straight and extend radially outward from the center post when the fixation devices are in an open configuration; and first and second sails attached to the first and second fixation devices, respectively.

12. The occlusion device of claim 11 wherein an angle between each arm of the first and second fixation devices is about equal.

13. The occlusion device of claim 11 wherein a length of the arms of the first fixation device is not equal to a length of the arms of the second fixation device.

14. The occlusion device of claim 11 wherein at least one arm of the second fixation device has a length not equal to a length of the other arms of the second fixation device.

15. The occlusion device of claim 11 wherein the first fixation device is offset from the second fixation device at an angle of about 30 degrees.

16. The occlusion device of claim 11 wherein the arms have diameters between about 0.003 inches to about 0.050 inches.

17. The occlusion device of claim 11 and further comprising holes in the center post through which the first and second fixation devices extend.

18. The occlusion device of claim 11 wherein the first and second fixation device comprise eight arms.

19. The occlusion device of claim 11 wherein the first and second fixation devices comprise ten arms.

20. The occlusion device of the claim 11 wherein the number of sides of the first and second sails is equal to the number of arms of the fixation devices.

21. An occlusion device deliverable through a catheter, the occlusion device comprising:

a center post;

a first fixation device configured to be placed on a first side of a septal defect and having an open configuration and a folded configuration, the first fixation device comprising at least five arms, each arm including an atraumatic tip located at an outer end; and a second fixation device configured to be positioned on a second side of a septal defect and having an open configuration and a folded configuration, the second fixation device comprising at least five arms, each arm including an atraumatic tip located at an outer end; and wherein the arms of the first and second fixation devices have lengths such that when the arms are in a collapsed position for delivery through the catheter, the atraumatic tips located at the outer ends of the arms are at staggered locations, and wherein the arms are generally straight and extend radially outward from the ceter post when the fixation devices are in an open configuration.

22. The occlusion device of claim 21 wherein a length of the arms of the first fixation device is not equal to a length of the arms of the second fixation device.

23. The occlusion device of claim 21 wherein the arms of the first fixation device are not all of equal length.

24. The occlusion device of claim 23 wherein the arms of the second fixation device are not all of equal length.

25. The occlusion device of claim 21 wherein a diameter of the arms is about 0.003 inches to about 0.050 inches.

26. The occlusion device of claim 21 wherein the first fixation device is offset at an angle of about 30 degrees from the second fixation device.

27. The occlusion device of claim 21 wherein each arm is spaced at an equal angle from the adjacent arm.

28. The occlusion device of the claim 21 and further comprising first and second sails attached to the first and second fixation devices.

29. The occlusion device of claim 21 wherein the first and second fixation devices comprise six arms.

30. The occlusion device of claim 21 and further comprising a center post to which the first and second fixation devices are attached.

31. The occlusion device of claim 21 wherein the arms of the first and second fixation device are formed to have a stiffness that ensures proper occlusion of the defect and provides the desired tension, yet does not decrease fatigue life of the fixation devices.

32. An occlusion device for occluding a septal defect, the occlusion device comprising:

a center post;

a first fixation device configured to be placed on a first side of a septal defect and having an open configuration and a folded configuration, the first fixation device comprising a plurality of arms which do not have equal lengths, each arm including an atraumatic tip at an outer end; and a second fixation device configured to be positioned on a second side of a septal defect and having an open configuration and a folded configuration, the second fixation device comprising a plurality of arms which do not have equal lengths, each arm including an atraumatic tip at an outer end; and wherein when the fixation devices are in a folded configuration the atraumatic tips do not cluster at a same location, and wherein the arms are generally straight and extend radially outward from the center post when the fixation devices are in an open configuration.

33. The occlusion device of claim 32 wherein the length of the arms of the first fixation device is not equal to the length of the arms of the second fixation device.

34. The occlusion device of claim 32 wherein the plurality of arms comprises five arms.

35. The occlusion device of claim 32 wherein the plurality of arms comprises six arms.

36. An improved occlusion device, the occlusion device comprising:

a center post;

first and second fixation devices connected to the center post and having an open configuration and a folded configuration, the first and second fixation devices and comprising at least five arms, each arm having an atraumatic tip at an outer end, wherein the arms of the first fixation device are not all of equal lengths so that when the fixation devices are in a folded configuration the atraumatic tips do not cluster at the same location, and where the arms are generally straight and extend radially outward from the center post when the fixation devices are in an open configuration; and first and second sheets attached to the first and second fixation devices respectively.

37. The occlusion device of claim 36 wherein the arms of the second fixation device are not all of equal lengths.

38. The occlusion device of claim 36 wherein each of the first and second fixation devices comprises six arms and a first arm and a fourth arm of the first fixation device have a first length, a second arm and a fifth arm of the first fixation device have a second length, and a third arm and a sixth arm of the first fixation device have a third length.

39. The occlusion device of claim 38 wherein a first arm and a fourth arm of the second fixation device have a first length, a second arm and a fifth arm of the second fixation device have a second length, and a third arm and a sixth arm of the second fixation device have a third length.

40. An improved occlusion device, the occlusion device comprising:
   a center post; and
   first and second fixation devices connected to the center post and having an open configuration and a folded configuration, the first and second fixation devices each comprising six arms, each arm including an atraumatic tip at an outer end, wherein the six arms extend through holes in the center post and the arms of at least one fixation device are not all of equal length so that when the fixation device is in a folded configuration the atraumatic tips do not cluster at a same location, and wherein the arms are generally straight and extend radially outward from the center post when the fixation devices are in an open configuration; and
   first and second sheets attached to the first and second fixation devices respectively.

41. The occlusion device of claim 40, wherein the six arms are formed by three wires.

42. An occlusion device for occluding a septal defect, the occlusion device comprising:

a center post;

a first fixation device configured to be placed on a first side of a septal defect and having an open configuration and a folded configuration, the first fixation device comprising at least five arms, each arm including an atraumatic tip at an outer end, wherein the arms of the first fixation device are not all of one length so that when the fixation device is in a folded configuration the atraumatic tips do not cluster at the same location, and wherein the arms are generally straight and extend radially outward from the center post when the fixation devices are in an open configuration; and a second fixation device configured to be positioned on a second side of a defect and having an open configuration and a folded configuration, the second fixation device comprising at least five arms, each arm including an atraumatic tip at an outer end, wherein the arms of the second fixation device are not all of one length so that when the fixation device is in a folded configuration the atraumatic tips do not cluster at the same location, and wherein the arms are generally straight and extend outward from the center post when the fixation devices are in an open configuration.

* * * * *

UNITED STATES PATENT AND TRADEMARK OFFICE
CERTIFICATE OF CORRECTION

PATENT NO. : 7,115,135 B2
APPLICATION NO. : 10/348701
DATED : October 3, 2006
INVENTOR(S) : Michael P. Corcoran et al.

It is certified that error appears in the above-identified patent and that said Letters Patent is hereby corrected as shown below:

Column 1, Line 28 delete "ovate", insert --ovale--

Column 5, Line 18, delete "0.001", insert --.001--

Column 5, Line 21, delete "0.003", insert --.003--

Column 5, Line 21, delete "0.050", insert --.050--

Column 5, Line 18, delete "and 10 increase", insert --and increase--

Column 5, Line 63, delete "arm in", insert --arm. In--

Column 6, Line 58, delete "method, Such", insert --method, such--

Column 9, Line 32, delete "device of the claim", insert --device of claim--

Column 9, Line 54, delete "ceter post", insert --center post--

Column 10, Line 3, delete "device of the claim", insert --device of claim--

Column 12, Line 23, delete "extend outward", insert --extend radially outward--

Signed and Sealed this

Twenty-seventh Day of March, 2007

JON W. DUDAS
*Director of the United States Patent and Trademark Office*